United States Patent [19]

Meinke et al.

[11] 4,184,492

[45] Jan. 22, 1980

[54] SAFETY CIRCUITRY FOR HIGH FREQUENCY CUTTING AND COAGULATING DEVICES

[75] Inventors: Hans H. Meinke, Gauting; Gerhard Flachenecker, Ottobrunn; Karl Fastenmeier; Friedrich Landstorfer, both of Munich; Heinz Lidenmeier, Planegg, all of Fed. Rep. of Germany

[73] Assignee: Karl Storz Endoscopy-America, Inc., Los Angeles, Calif.

[21] Appl. No.: 910,963

[22] Filed: May 30, 1978

Related U.S. Application Data

[63] Continuation of Ser. No. 709,609, Jul. 29, 1976.

[30] Foreign Application Priority Data

Aug. 7, 1975 [DE] Fed. Rep. of Germany ....... 2535341

[51] Int. Cl.² .................. A61B 17/36; A61N 3/02
[52] U.S. Cl. ................... 128/303.14; 128/303.17; 128/908

[58] Field of Search ............ 128/303.13, 303.14, 128/303.15, 303.17, 303.18, 2.1 P

[56] References Cited

U.S. PATENT DOCUMENTS

| | | | |
|---|---|---|---|
| 3,478,774 | 11/1969 | Leiter | 128/303.14 |
| 3,601,126 | 8/1971 | Estes | 128/303.14 |
| 3,683,023 | 8/1972 | Anderson | 128/303.14 |
| 3,706,008 | 12/1972 | Kremer | 128/2.1 P X |
| 3,804,096 | 4/1974 | Gonser | 128/303.14 |
| 3,838,242 | 9/1974 | Goucher | 128/2.1 P X |
| 3,905,373 | 9/1975 | Gonser | 128/303.14 |
| 3,913,583 | 10/1975 | Bross | 128/303.14 |

*Primary Examiner*—Lee S. Cohen
*Attorney, Agent, or Firm*—Donald D. Mon

[57] ABSTRACT

In a surgical system for high frequency electrical cutting and cauterizing circuitry to prevent stray currents from harming the surgeon or the patient. This circuitry provides a preferred path for undesirable currents, and to indicate to a surgeon when the undesirable currents are too intense.

20 Claims, 11 Drawing Figures

SAFETY CIRCUITRY FOR HIGH FREQUENCY CUTTING AND COAGULATING DEVICES

CROSS-REFERENCE TO CO-PENDING APPLICATION

This is a continuation of applicants' co-pending patent application, Ser. No. 709,609, filed July 29, 1976, now abandoned, which at the time of filing was entitled: "Means to Protect the Patient and the Surgeon from Stray Electrical Currents".

This invention concerns a device for cutting and/or coagulation of human tissue during surgery, with the use of a high frequency current.

A device according to the invention comprises: a high frequency generator; a unit, the parts of which are produced totally or only partly of conductive materials; and a probe which is held or guided by the unit that serves for cutting and/or coagulation. This probe is insulated from the conductive parts of the unit. Furthermore, this device includes a conductive connection between one output contact of the high frequency generator and the probe, and another conductive connection between the second output contact of the high frequency generator and an electrode. This electrode produces a high frequency current connection, i.e. a capacitative connection, with the body of the patient. Insulated probes are already being used in the surgical field, i.e. when the human tissue is to be cut in such areas as can be reached through natural openings (without surgical opening of the body of the patient). Examples are operations inside the bladder or on the prostate. But, because of the styptic (blood-staunching) effect of the high frequency current, such instruments also will be used frequently when human tissue is to be cut or coagulated on the surface of the body or after surgical opening of the body.

This invention will be fully understood from the following detailed description and the accompanying drawings in which.

Figure 1:
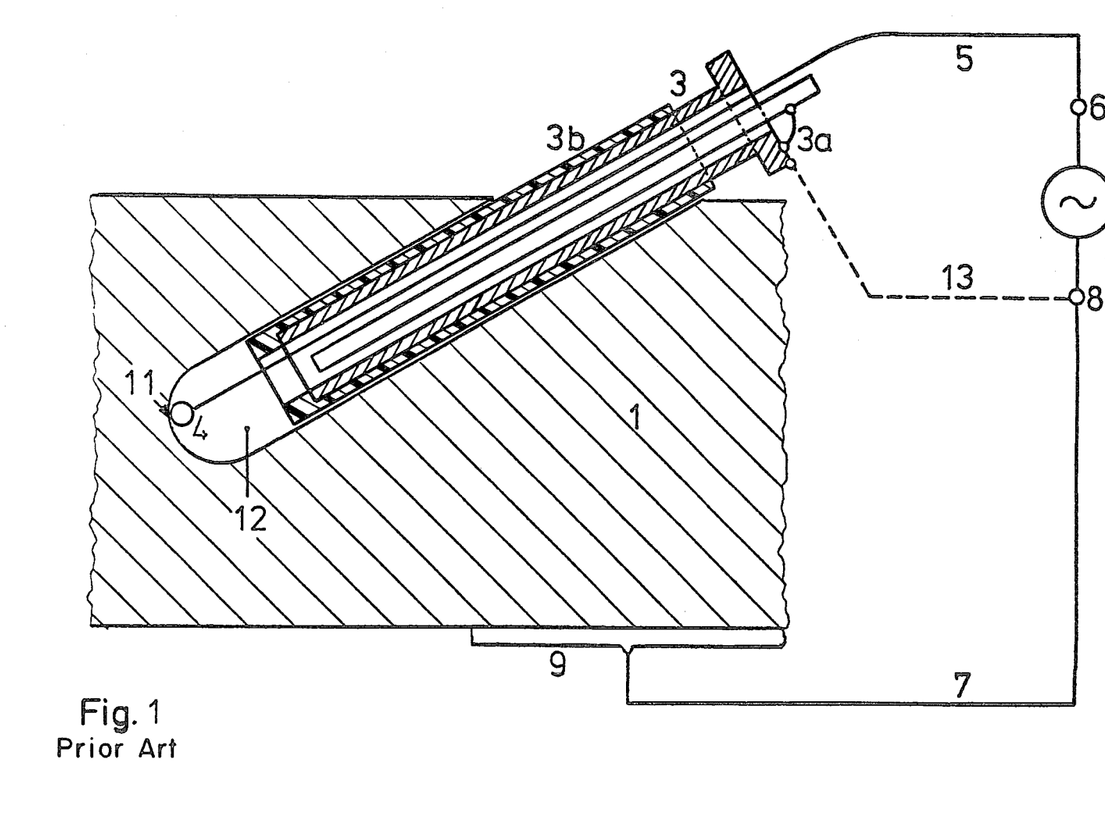
FIG. 1 is a side view partly in schematic, and partly in cutaway cross-section, showing a prior-art situation.

FIG. 1 shows, as an example, the schematic construction of a device for the cutting and/or coagulation of human tissue with the use of a high frequency current. Human tissue 1 is schematically illustrated to show the specific area of the body of the patient at which a cutting and/or coagulation process is to be performed. The output contact 6 of a high frequency electrical current generator 2 is attached via an electrical lead 5 to a probe 4, which serves for cutting and/or coagulation. Another electrical lead 7 connects a second output contact 8 of the high frequency generator to an electrode 9 which often is of flat structure. Electrode 9 establishes a connection for the high frequency current to the body of the patient. The connection established by electrode 9 can be either a galvanic or a capacitive type.

In the illustrated example, one presumes that the field of operation 11 in which the cutting and/or coagulation is to take place, is not located on the surface of the body of the patient, but that it can be reached through a natural opening (i.e. through the urethra). Probe 4 must be driven through the tissue for cutting, or has to be brought into contact with the surface of the tissue for coagulation. For this purpose it is held by a mechanism 3 (sometimes called a "unit"). In addition to holding the probe, this mechanism is also capable of performing other duties. It can be used, if necessary, to open and hold open the incision, thus making it possible to insert the probe. In these cases the guidance of the probe is usually also performed by this mechanism. The probe is then movable respective to the mechanism and can therefore cover (in the immediate proximity of the nearly immobile mechanism) a substantial field of operation. This mechanism is equipped in many cases, with an optical device, with the help of which the operating field can be illuminated and observed by the operating surgeon. This mechanism often also performs the duty of transporting irrigating fluid to and from the operating field. The operating field can be rinsed with fluid in case the eventuality arises that profuse bleeding occurs.

If the diameter of the body opening is so small, as in the case of the urethra, that the maximum allowable diameter of the device is limited to a few millimeters, then the mechanism has to be built to a large extent of metallic, electrically conductive, materials 3a to provide sufficient mechanical stability, and also to provide structure for the other expected duties it has to perform. Additional, today the only known optical devices are those which are totally housed inside a metal tube. In fact for the above reasons, many of the mechanisms of this kind which are in use today are produced almost totally of metal, even parts of the mechanism which touch the body of the patient, as for example the urethra, and parts which are held by the operating surgeon and which for reasons of observation are brought close to the eye of the surgeon. It sometimes happens that after the using of these devices the patient incurs destruction of tissues that had not been touched by the probe, but were in contact only with electrically conducting parts of the mechanism. It has happened, for example, that patients with transurethral resection of prostate tissue or bladder tumors have suffered strictures or stenoses of the urethra after being treated with such devices, although the adversely affected parts of the body are removed from the real operating field. They merely happened to be in an area that was being touched by the mechanism. It occurs fairly often that the operating surgeon suffers an electrical shock, or even an injury, from the high frequency currents or sparks that discharge and which arc from the mechanism to the body of the surgeon. These grave consequences of operations are being discussed in detail by the medical association, and different theories have been developed to explain these incidents. Besides the suspicion that these injuries of the patient are caused by purely mechanical means, it has been surmised until recently that such injuries are at least partly due to the heating effect of the high frequency current, which passes over from the mechanism into those parts of the body (i.e. the urethra) that are being touched by the mechanism during the cutting or coagulation process.

It was thought until now that the cause of such a high frequency current is the capacity between the electrical leads to the probe (located in the mechanism), and the conductive parts of the mechanism; e.g. see the report of the German Urological Association, 26. convention in Munich 1974, page 44–51. The above mentioned high frequency currency is therein designated as leakage-current. It was suggested (and in some designs realized) to reduce the capacity between the lead 5 leading to the probe and the mechanism 3a, constructed of conductive material with different already-known means, for relief. As further means for relief it was suggested to lessen the operating frequency, whereby the capacitive currents diminish.

Another remedy was thought to be of help: to insulate all the metallic parts of the mechanism which would come in contact with the patient, and cover them with insulating layers (see 3b in FIG. 1). However, this does not protect the patient in case of undetected damage of the insulating layers, which layers must be thin-walled because of bulk considerations. Punctiform damages lead to especially serious burn injuries, due to the concentrations of the current. The surgeon was noted to be endangered also. In the U.S.A., where these insulated mechanisms are in extensive use, the characteristic burns on the foreheads of urologists are known jokingly as a trademark of the profession. The problem was thought to have been solved by connecting the metallic parts 3a of the device with an additional electrically connecting lead 13 to the second output contact 8 of the high frequency generator. This did solve the problem from the surgeon, but the patient was again endangered by burns, as experience showed.

It is an objective of this invention to fashion this device for cutting and/or coagulation of the human tissue in such a way that the above mentioned dangers for both patient and surgeon will be avoided.

This problem is solved (FIG. 2) by this invention in such a manner that, for the protection of the patient and of the operating surgeon, some or all of the conductive parts 3a of the mechanism are electically connected to second output contact 8 of the high frequency generator through an additional circuit 10. The additional circuit is designed in such a way that within a connection lead 25, an impedance (Z) of at least 100 ohms is produced. Furthermore, the additional circuit 10 may be adapted to measure the current flowing through lead 25, or the voltage produced over the impedance of the additional circuit by this current, respectively, and indicate an excess over a predetermined safe value.

This invention is based on extensive observations of operating procedures, and of detailed measuring of the flow of high frequency currents. Furthermore, the different branch-currents have been measured on models of the human body for direction and intensity. In this way the inventors produced the schematic circuit diagram of FIG. 2, which represents the basis for the additional circuit.

Figure 2:
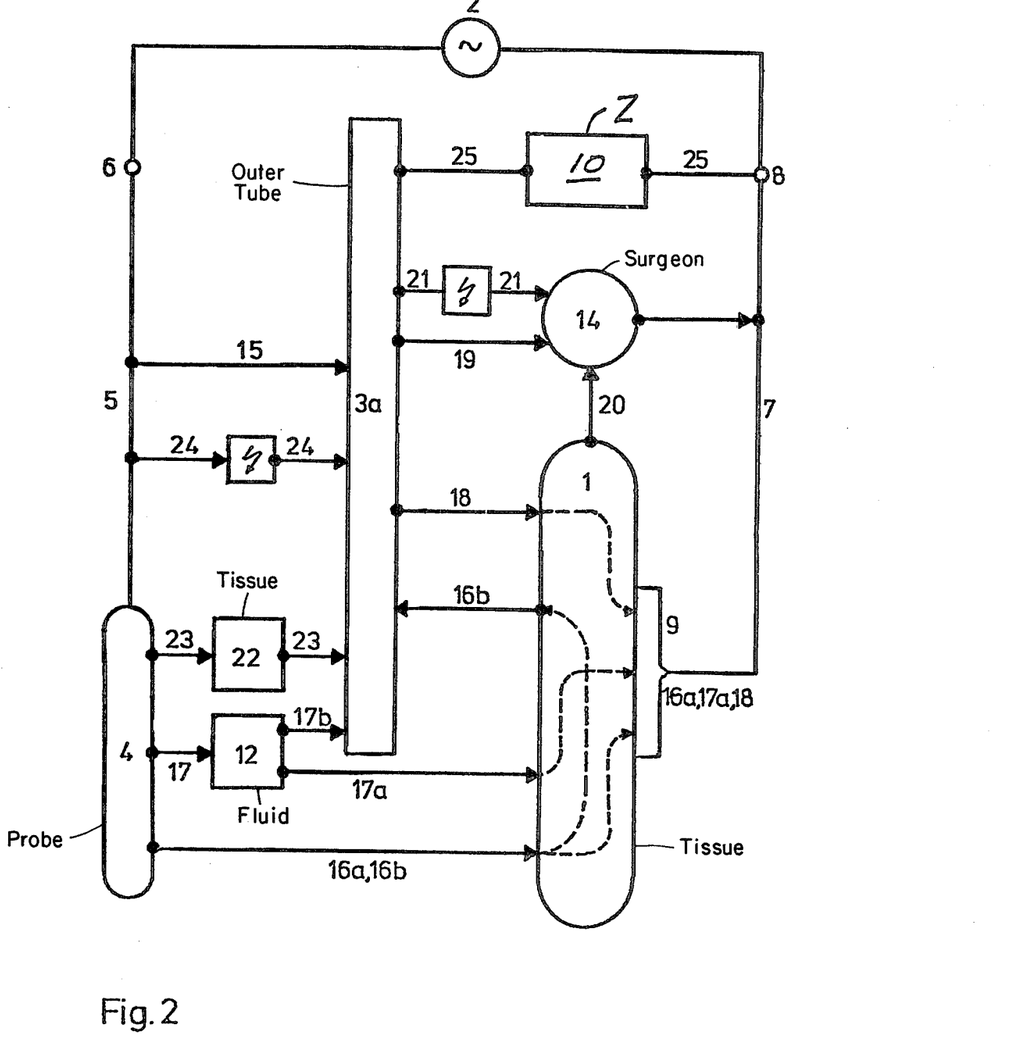
FIG. 2 is a schematic circuit analysis indicating various current paths which may exist in high frequency cutting and cautery.

FIG. 2 schematically shows, using the same numbers as in FIG. 1, the capacitive current 15 between the lead 5 of probe 4 and the metallic parts 3a of the mechanism. The inventors have discovered, to the contrary of the prevailing opinion, that these capacitive currents are harmless in their effect, due to their low intensity in the normally used mechanisms.

In FIG. 2, more circuits are illustrated that were discovered to exist during the respective research: the currents 16a and 16b that flow into the human tissue from the probe during the cutting and/or coagulation process. These do not flow uniformly to the electrode 9. Rather, one part 16a flows to the electrode 9 directly, and one part 16b first flows to the conductive parts 3a. If fluid is present for rinsing, a branch-current 17 forms that flows partly as current 17b from the probe, through the fluid 12 to the conductive parts 3a, and partly as current 17a from the probe through the fluid into tissue 1.

Figure 3:
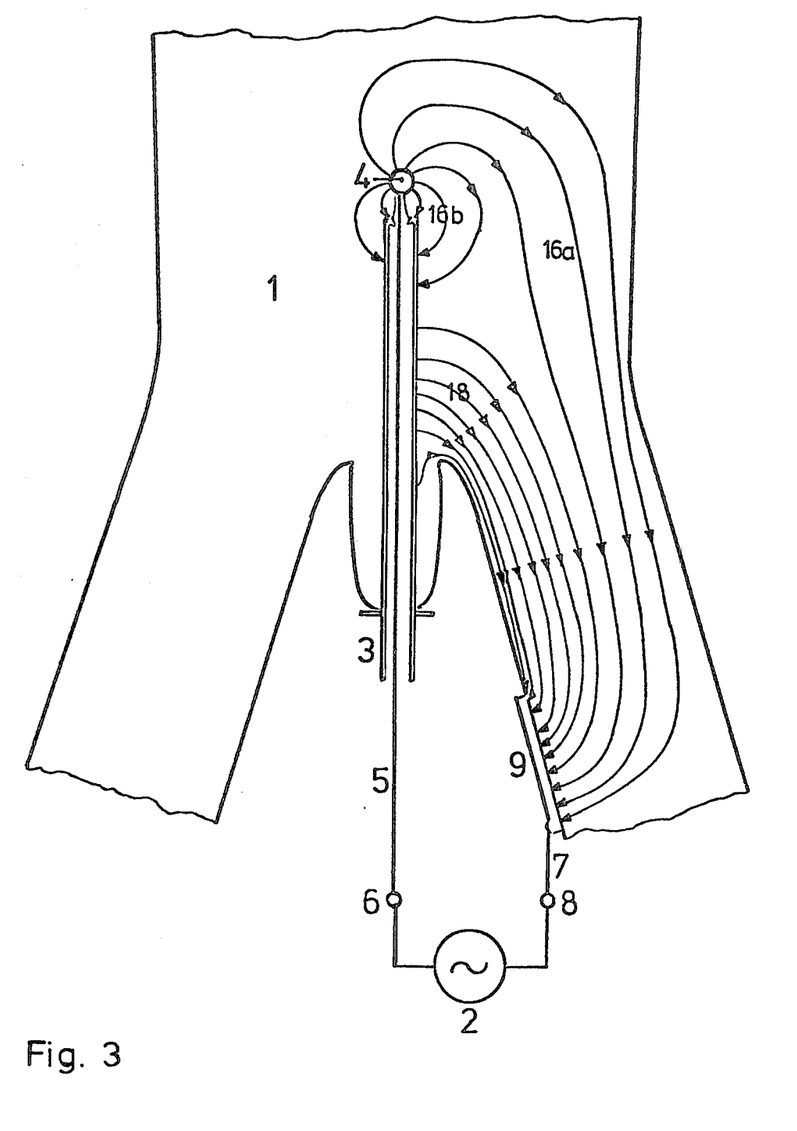
FIG. 3 is a schematic axial section showing some possible current paths.

The currents that flow to the conductive parts 3a flow to a large extent through the current-branch 18 into tissue 1, and from there out through the electrode 9 (FIGS. 2 and 3). Because of current-flow present in the human tissue, and owing to the relatively slight conductivity of the human tissue, the described process is always associated with the establishment of voltage. There is a damming up of voltage between the individual parts of the mechanism, especially between the probe 4 and the electrode 9, and also between the probe 4 and the conductive parts 3a, and also between the electrode 9 and the conductive parts 3a. The surgeon 14 must hold and attend the mechanism 3. Also, he is generally in contact with the operating table and the other surroundings. Because of this, he is very frequently connected with the second output contact 8 of the high frequency generator. If the surgeon 14 touches the body of the patient during the operation, the current 20 will flow over through the point of contact.

If a device is used in which all the conductive parts 3a of the mechanism are completely insulated from the body of the patient, then the current-branches 16b and 18 which develop are relatively weak, because the currents in question only can flow capacitively to the conductive parts. If rinsing fluid is present, however, then the flow of the high frequency current that flows to the conductive parts is relatively large. Then it can only flow through the surgeon, as current 19. If the contact area between the surgeon and the device is only a small spot, for example, the point of contact with the forehead of the surgeon during observation of the operating field through the ocular piece of the optical unit, and if the surgeon wears insulating gloves to handle the mechanism, the current can pass over to the surgeon in the form of a spark discharge of relatively high intensity. Such a current is shown in FIG. 2 and is numbered 21. FIG. 3 shows why the total current that flows between the conductive parts 3a and the human tissue 1 in FIG. 2 divides into parallel current-branches 16b and 18. This example of an operation on the prostate gland is illustrated to serve as an example to explain what takes place in a typical operation.

The device 3 is inserted into the urethra, so that the probe 4 can be brought close to the tissue to-be-cut or to-be-coagulated tissue. The high frequency current that is produced by the high frequency generator is connected mainly by way of the conductive lead 5, to the probe 4, and flows from there through the human tissue 1 to the electrode 9, and through conductive lead 7 back to the high frequency generator. The sum of the flowing high frequency currents 16a, 16b, 17a and 18 which flow from the probe 4 to the electrode 9 spread through the human tissue 1 of the patient in the form of a complicated current-field, as is indicated in FIG. 3, where arrows point out the generalized direction of the current lines.

If the mechanism 3 would not exist, or if it would be totally non-conductive, then the total high frequency current derived from the probe 4 would go through the human tissue as current 16a, directly to the electrode. If a mechanism consisting of metallic conductive parts 3a is introduced into the current-field, then a large part, 16b, of the high frequency current which is derived from the probe primarily flows to the conductive parts 3a of the mechanism in order to leave these parts 3a at another location located closer to the electrode 9; as current 18 then travels through the human tissue and from there to the electrode. Extensive measurements during operations on human bodies and during experiments with models have proven that the part 16b of the high frequency current that flows over the conventional mechanism (made of metallic materials) can be higher than 50% of the total current that flows from the probe 4 into the human tissue 1 and is a considerable source of danger, unrecognized until now.

The high frequency currents 16b and 18 that flow between the conductive parts 3a of the mechanism 3 and the human tissue 1 heat the human tissue according to the different current densities existing at the points of contact. With today's normally used mechanisms and normal conditions during an operation procedure, the above mentioned heating remains below the limit where dangerous results occur in the vicinity of the mechanism. Normal conditions exist when the duration of the operation does not exceed normal average time, if the surgeon does not adjust the output of the high frequency generator in such a way that it is higher than is absolutely necessary for cutting and/or coagulating, and if no poor conducting or insulating lubricating means is being used as a layer between the mechanism and the tissue. In contrast, during the observations of real operations and especially during experiments with models of the human body the inventors found statistical events, wherein the current 18 passing from the conductive parts 3a to the human tissue 1 increased to very high values. These burst-like events generally took place unnoticed by the surgeon but generated amounts of heat which are destructive to human tissue. Such an event happened, for example, when a severed part of tissue 22 (FIG. 2) that was cut by the probe 4 lodged between the probe 4 and one of the conductive parts 3a of the mechanism. In that case a current 23, illustrated in FIG. 2, flows from the probe 4 to the conductive parts 3a. This value of the current can be as much as already equal to the total output value of the current that the high frequency generator delivers.

Similar conditions arise if a discharge occurs between the lead 5 and the conductive parts of the device, due to an insulation failure or because of the presence of moisture. Also they may arise if the probe 4 was accidentally deformed in such a way that it is close enough to the conductive parts so that a galvanic contact is made, or respectively close enough to cause a discharge. The current which is such cases flows to the conductive parts can be assumed to be the value of the total output current of the generator and is shown in FIG. 2 and marked with the number 24.

At the occurrence of the above described unwelcome events, the large high frequency current that flows to the conductive parts 3a has to be conducted from the conductive parts 3a to the connection 8 of the high frequency generator, through the already existing current channels. If the connecting parts of the device are not insulated from the body of the patient, then this current flows mainly in the form of the currents 18 in FIG. 2 through the human tissue to the electrode 9 and back to the high frequency generator. At the cross-over of the current 18 from the conductive parts 3a to the human tissue, heat develops because of the high current value that can lead to damage of the tissue. If the conductive parts are insulated against the patient's body, then this current can cross over only to the surgeon in the form of the current 19 or in the form of a spark discharge 21. The inventors have found that the endangering of the patient or the surgeon occurs mainly in such moments in which the voltage of the conductive parts 3a respective to the tissue 1 or to the surgeon 14 is high and therefore, theoretically, the possibility of large currents through patient or surgeon exists. In an extreme case, where insulation exists between the conductive parts 3a and the patient, the high currents endanger the surgeon only. At the other extreme case if, through the already mentioned short circuit 13 between 3a and 8 no voltage exists between 3a and 14, the high currents endanger the patient only. In the later case, a high current value mainly on the path 16b develops, because there it finds a path of relatively small resistance, over the conductive parts 3a and the shorting path 13.

The additional circuit 10 with its connection 25, serves, according to this invention, to observe and influence the voltage between the conductive parts 3a and the second output contact of the generator 8 which was discovered to be the source of danger, in such a way that the dangerous voltage will, in the broader sense be lessened or prevented. The additional circuit 10 establishes an impedance (Z) in the connection 25 that should not be a short circuit, for reasons mentioned in the above explanation. Therefore the impedance (Z) has to be above a lower value limit. Many measurements in real situations have shown the result that, in the arrangement illustrated in FIG. 2, the existing impedance between the output contacts 6 and 8 of the high frequency generator, when no additional circuit 10 exists, always comes to values between 300 and 1000 ohms. If the additional circuit 10 is not to act as a short circuit, then the impedance of the circuit 10 cannot be more than one order to magnitude lower than the above mentioned values of the impedance. Experimentally, a lower limit of 100 ohms was selected with these considerations in mind.

In many designs of this invention the additional circuit 10 is fashioned in such a way that it develops in the connection 25 an impedance lower than 1000 ohms. Such an impedance in general is relatively small in comparison with the impedance the surgeon represents for the current paths 19, 20 and 21, whereby the currents that flows through the surgeon 14 diminish noticeably. Especially in designs in which the conductive parts 3a of this mechanism are completely insulated from the body of the patient, relatively high voltages could occur between the conductive parts and the surgeon, even by currents 15, 16b, 17b, 23 and 24 of low intensity if the impedance of the additional circuit would be much higher than 1000 ohms.

A design with a predetermined impedance of the circuit 10 cannot prevent an endangering of the patient or surgeon in a few cases of especially large currents 23 or 24. In an improved design of this invention the current that flows through the circuit 10 is measured, or a voltage that has developed in the circuit 10 is measured, and the exceeding of a prespecified value limit is indicated. In the simplest case this reading will tell the operating surgeon that he should interrupt the high frequency current, or diminish it, and search for the reasons of this exceeding of the limit.

Figure 4:
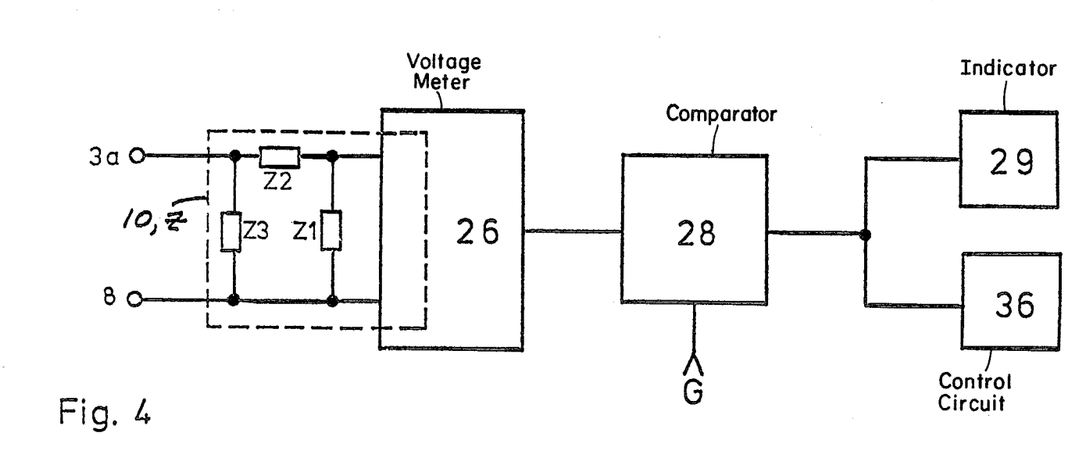
FIGS. 4–11 show various circuit details which are useful with this invention.

FIG. 4 shows possibilities for the design of the impedance (Z) of circuit 10 and the connection of a voltage meter 26. The impedance (Z) can consist formally of three impedances (Z1), (Z2), (Z3) in the $\pi$ (pi) circuit, or can have such an equivalent circuit diagram whereby it is possible that Z2=0 and/or Z3=$\infty$.

In the case Z2=0 the voltage meter 26 is located between the points of attachment 3a and 8, and measures the total voltage that exists in the circuit 10. If Z2 does not disappear, then the voltage meter measures only that part of the voltage which is being produced by the voltage distributor consisting of Z1 and Z2. The equivalent circuit diagram can even be a transformer.

Figure 5:
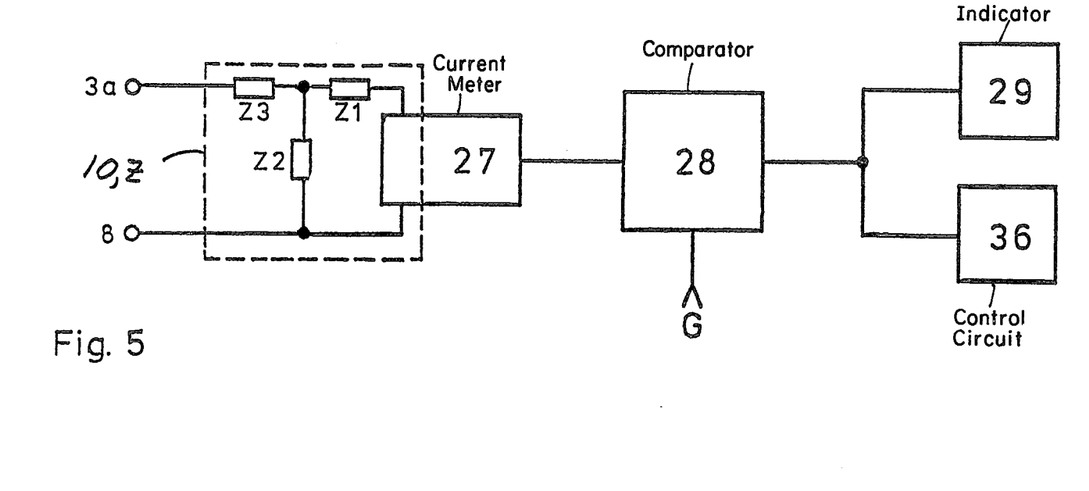

FIG. 5 shows possibilities for the design of the impedance Z for circuit 10 and the connection of a current meter 27. The impedance Z can consist of 3 impedances (Z1), (Z2), (Z3) in T circuit or possess such an equivalent circuit diagram whereby it is possible that $Z2=\infty$ and/or $Z3=0$. In the case $Z2=\infty$ the total current of the circuit 10 flows through the ammeter. If Z2 possesses finite values, then the ammeter measures only a part of the current.

Since there are dangers, both for the patient as well as for the surgeon only if certain value limits are exceeded, a device according to this invention may be set up so as to give readings only when these limits are being exceeded. At the output point of the voltage meter, in FIG. 4, or at the output point of the ammeter in FIG. 5, a test data comparison circuit 28 is placed in the circuit according to a preferred but optional feature of the invention.

Figure 6:
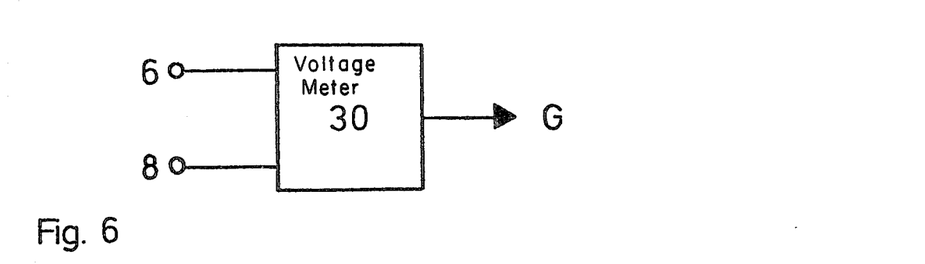
Figure 7:
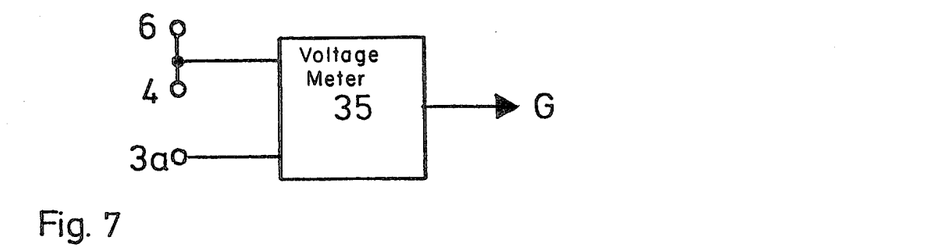
Figure 8:
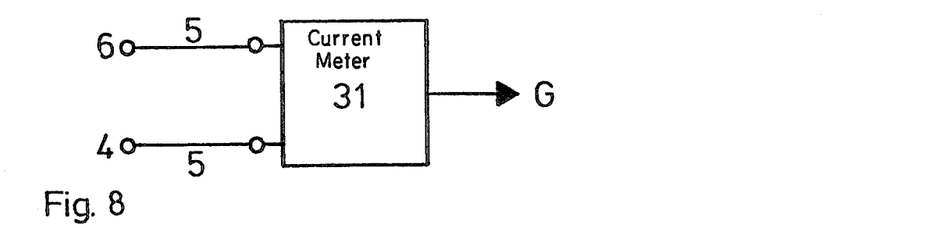
Figure 9:
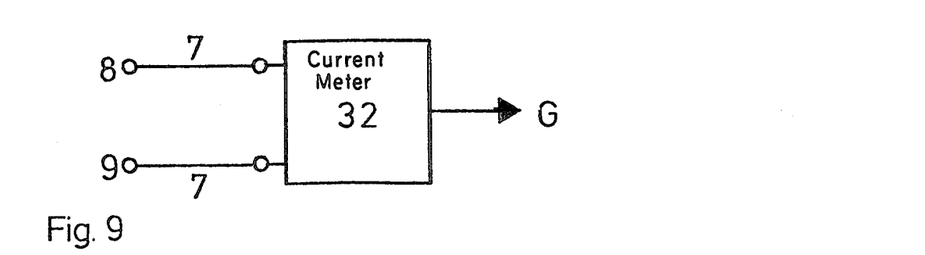

This test data comparison circuit is designed in such a way that one can preset a value limit (g). This value limit is compared with the measured voltage and/or current value and in case of exceeding the value limit, a signal is triggered in an indicator device 29 of any desired type. In the simplest case, the value limit is preset by the attending personnel to a constant predetermined value limit. In other cases it may be fashioned in such a way that the value limit is derived through characteristic voltages or currents of the system via further measurements. For example, another voltage meter 30 (FIG. 6), or current meter 31 (FIG. 8), or current meter 32 (FIG. 9) that measures the voltage produced by the high frequency generator between the points 6 and 8 or the current derived from the high frequency generator through connection 5 or connection 7, or a proportioned part of these values is measured and a value (G) is deduced as can be seen from FIGS. 6, 8 and 9. In another example (FIG. 7) a proportioned part of the existing voltage between the probe 4 and the conductive parts 3a can be measured by a voltage meter 35. This value limit G derived in this way is the introduced into then test data comparison circuit 28 (FIGS. 4 and 5).

If one takes the value limit (G) of a characteristic electrical value (voltage or current) of the circuit-system of FIG. 2, and compares it with the current value of the additional circuit 10 with a test data comparison circuit 28, then this comparison gives as result a reading of the condition of the impedances of the current system. Then exceeding the value limit indicates that the condition of the impedance has changed in an unpermissive way e.g. through sparks on the paths 21 or 24, or through a severed piece of tissue 22.

Figure 10:
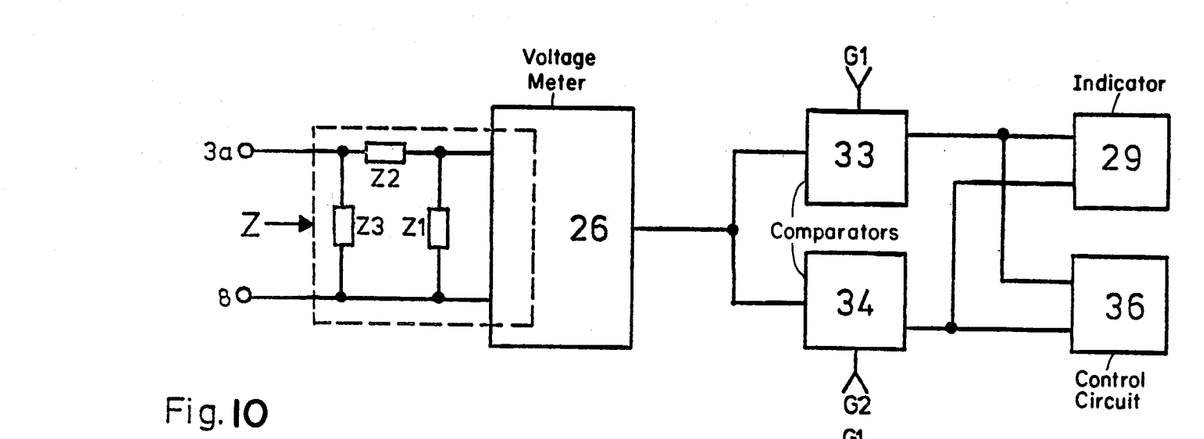
Figure 11:
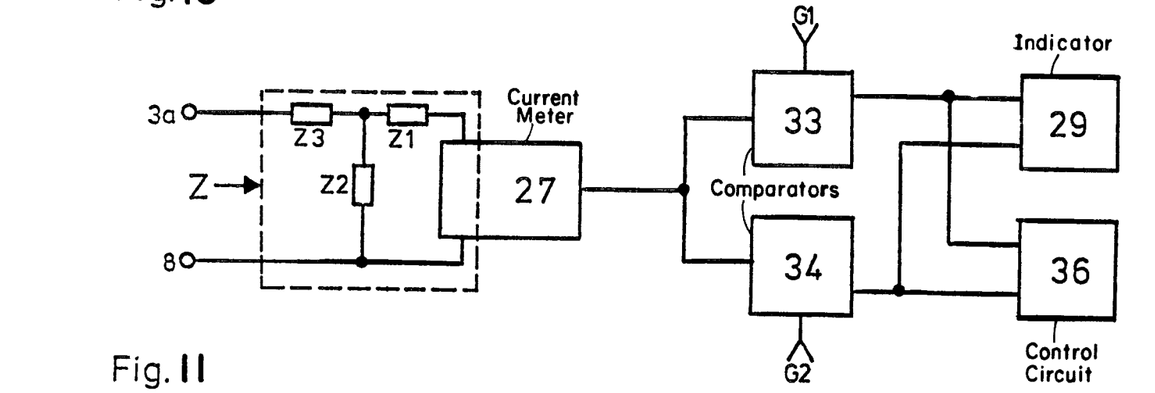

In a useful form of the design of this invention the two value limit criteria (the constant value limit and the value limit that is derived from characteristic voltages or currents of the circuit) can both be utilized at the same time. The constant value limit serves hereby as a maximum limit that cannot be surpassed for any reason (because it is dangerous under all circumstances). As long as the value of the circuit system does not reach this upper limit, then the other value limit criterion is in use, whereby it registers only changes of the impedances that are allowable. In the simplest case then the value limit (G) produced by a voltage meter 30 or 35, or a current meter 31 or 32 is only up to an upper limit. After reaching this upper limit the value limit (G) remains constant and equal to this upper limit even when the respective voltage or current increases. This reaction of the circuit can be obtained as follows: for the voltage-comparison (FIG. 10) and/or for the current-comparison (FIG. 11), two test data comparison circuits 33 and 34 are employed. The first data comparison circuit receives the constant limit value (G2) which is proportional (as described above) to a characteristic electrical value of the circuit. The test data comparison circuits are fashioned in such a way that each registers into the indicator device 29 independently. The circuits may "buck" each other, and an appropriate excess signal can set off an alarm, for example.

It is advantageous for most designs of this invention to have the indicator device arranged in such a way that it gives off a signal that is easily recognized by the surgeon. This indicator can be employed in such a way that the operating surgeon does not have to adjust, but that, with the help of a control circuit 36, the energy derived from the high frequency generator can be lessened or completely shut off. This lessening of the energy should take a certain time (at least a second), with the help of a time switch to give the surgeon enough warning to recognize and eliminate the exceeding of the value limit.

The parameters of the various systems can readily be determined by persons skilled in the art. It is customary to use the usual probe with a power supply that operates at about 1.7 MHz, 250 volts, and up to one ampere. The circuit 10 should have an impedance not less than 100 ohms with practical surgical instruments, for example, with a Storz Resectoscope, for example, a 27040C, D or E type. An appropriate setting G would tend to be about 20% of the generator output voltage. For an absolute limit, it would be about 60 volts.

This invention is not to be limited by the embodiments shown in the drawings and described in the description, which are given by way of example and not of limitation, but only in accordance with the scope of the appended claims.

We claim:

1. In combination: apparatus for the surgical cuttting and/or coagulation of tissue, said apparatus being adapted to utilize high frequency electrical currents derived from a generator of high frequency electrical current, said generator having a first and a second output contact, said apparatus including an outer tube whose outer surface is at least partially made of metallic conductive material intended in use to be in conductive contact with tissue inside the human body, a conductive probe functioning as an electrode supported by, but insulated from, the conductive portions of said outer tube, a second electrode detached from said outer tube and probe and intended to remain outside the human body in conductive contact with said human body, a first conductive lead means for interconnecting the first contact to the probe, and second conductive lead means for connecting the second contact to the second electrode; and safety circuit means conductively interconnecting the said metallic conductive material of said outer tube to said second conductive lead means, said safety circuit means providing an impedance not less than about 100 ohms, whereby said outer tube functions at a voltage intermediate between said contacts during normal operation as a consequence of current flow from said probe to said outer tube.

2. Apparatus according to claim 1 in which means is provided in said circuit means to measure and indicate the value of the voltage across, or the current which passes through, said circuit means.

3. Apparatus according to claim 2 in which a value limit is determined for said circuit means, and in which said circuit means includes means to signal when the said voltage or current exceeds said value limit.

4. Apparatus according to claim 3 in which said impedance is not greater than about 1,000 ohms.

5. Apparatus according to claim 3 in which value means is provided to determine said value limit, said value means including proportionalizing means to set the value limit as a percentage of the actual value of the output current or voltage of said generator, and also to limit the maximum value limit.

6. Apparatus according to claim 5 in which said impedance is not greater than about 1,000 ohms.

7. Apparatus according to claim 3 in which control means is provided which control the generator to reduce its current output when the value limit is exceeded.

8. Apparatus according to claim 3 in which the signal means is provided with latch means to hold the signal in operation for a period of time after the value limit was exceeded independently of the actual voltage or current in said circuit means.

9. Apparatus according to claim 3 in which said value limit is a constant maximum value which when exceeded causes said means to signal to function.

10. Apparatus according to claim 2 in which said impedance is not greater than about 1,000 ohms.

11. In combination: apparatus for the surgical cutting and/or coagulation of tissue, said apparatus being adapted to utilize high frequency electrical currents derived from a generator of high frequency electrical current, said generator having a first and a second output contact, said apparatus including an outer tube which is at least partially made of metallic conductive material, said outer tube being intended in use to be in contact with tissue inside the human body, a conductive probe functioning as an electrode supported by, but insulating from, the conductive portions of said outer tube, a second electrode detached from said outer tube and probe and intended to remain outside the human body in conductive contact with said human body, a first conductive lead means for interconnecting the first contact to the probe, and second conductive lead means for connecting the second contact to the second electrode, some portions of the metallic conductive material being subject to inclusion in an electrical circuit from the probe to tissue inside the human body into which the outer tube has been inserted or to the surgeon, either by direct contact therewith or through a substance which contacts said portion and said tissue or said surgeon; and safety circuit means conductively interconnecting the said metallic conductive material of said outer tube to said second conductive lead means, said safety circuit means providing an impedance not less than 100 ohms, whereby said outer tube functions at a voltage intermediate between said contacts during normal operation as a consequence of current flow from said probe to said outer tube.

12. Apparatus according to claim 11 in which means is provided in said circuit means to measure and indicate the value of the voltage across, or the current which passes through, said circuit means.

13. Apparatus according to claim 12 in which a value limit is determined for said circuit means, and in which said circuit means includes means to signal when the said voltage or current exceeds said value limit.

14. Apparatus according to claim 13 in which said impedance is not greater than about 1,000 ohms.

15. Apparatus according to claim 13 in which value means is provided to determine said value limit, said value means including proportionalizing means to set the value limit as a percentage of the actual value of the output current or voltage of said generator, and also the limit the maximum value limit.

16. Apparatus according to claim 15 in which said impedance is not greater than about 1,000 ohms.

17. Apparatus according to claim 13 in which control means is provided which control the generator to reduce its current output when the value limit is exceeded.

18. Apparatus according to claim 13 in which the signal means is provided with latch means to hold the signal in operation for a period of time after the value limit was exceeded independently of the actual voltage or current in said circuit.

19. Apparatus according to claim 13 in which said value limit is a constant maximum value which when exceeded causes said means to signal to function.

20. Apparatus according to claim 12 in which said impedance is not greater than about 1,000 ohms.

* * * * *